United States Patent
Li et al.

(10) Patent No.: US 10,386,328 B2
(45) Date of Patent: Aug. 20, 2019

(54) CHEMICAL SENSOR WITH AIR VIA

(71) Applicant: Life Technologies Corporation, Carlsbad, CA (US)

(72) Inventors: James Li, Taipei (TW); Jordan Owens, Austin, TX (US); James Bustillo, Castro Valley, CA (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 0 days.

(21) Appl. No.: 15/700,630

(22) Filed: Sep. 11, 2017

(65) Prior Publication Data

US 2018/0106756 A1    Apr. 19, 2018

Related U.S. Application Data

(60) Provisional application No. 62/385,399, filed on Sep. 9, 2016.

(51) Int. Cl.
*G01N 27/414* (2006.01)
*G01N 27/12* (2006.01)

(52) U.S. Cl.
CPC ....... *G01N 27/4148* (2013.01); *G01N 27/125* (2013.01); *G01N 27/128* (2013.01); *G01N 27/4143* (2013.01); *G01N 27/4145* (2013.01); *B01L 2300/0636* (2013.01)

(58) Field of Classification Search
CPC ............... G01N 27/414–4148; G01N 27/4148
See application file for complete search history.

(56) References Cited

U.S. PATENT DOCUMENTS

| | | | |
|---|---|---|---|
| 7,948,015 B2 | 5/2011 | Rothberg et al. | |
| 8,901,621 B1* | 12/2014 | Bai | G01N 27/403 |
| | | | 257/253 |
| 8,963,216 B2 | 2/2015 | Fife et al. | |
| 9,128,044 B2 | 9/2015 | Fife et al. | |
| 9,841,398 B2 | 12/2017 | Bustillo et al. | |
| 2014/0073039 A1 | 3/2014 | Chang et al. | |
| 2014/0191293 A1* | 7/2014 | Bustillo | G01N 27/414 |
| | | | 257/253 |
| 2014/0264470 A1* | 9/2014 | Fife | G01N 27/414 |
| | | | 257/253 |
| 2014/0264472 A1* | 9/2014 | Fife | G01N 27/414 |
| | | | 257/253 |
| 2016/0202209 A1 | 7/2016 | Barbee et al. | |

OTHER PUBLICATIONS

PCT/US2017/051010, International Search Report and Written Opinion, dated Nov. 17, 2017, 1-14.

* cited by examiner

*Primary Examiner* — Frederick B Hargrove

(57) ABSTRACT

In one embodiment, a chemical sensor is described. The chemical sensor includes a chemically-sensitive field effect transistor including a floating gate conductor having an upper surface, a first opening extending through a first material and through a portion of a second material located on the first material and a second opening extending from the bottom of the first opening to the top of a liner layer located on the upper surface of the floating gate conductor.

9 Claims, 8 Drawing Sheets

CHEMICAL SENSOR WITH AIR VIA

CROSS-REFERENCE TO RELATED APPLICATION(S)

This application claims benefit of U.S. Provisional Application No. 62/385,399, filed Sep. 9, 2016, which is incorporated herein by reference in its entirety.

FIELD OF THE INVENTION

The present disclosure relates to sensors for chemical analysis, and to methods for manufacturing such sensors.

BACKGROUND

A variety of types of chemical sensors have been used in the detection of chemical processes. One type is a chemically-sensitive field effect transistor (chemFET). A chemFET includes a source and a drain separated by a channel region, and a chemically sensitive area coupled to the channel region. The operation of the chemFET is based on the modulation of channel conductance, caused by changes in charge at the sensitive area due to a chemical reaction occurring nearby. The modulation of the channel conductance changes the threshold voltage of the chemFET, which can be measured to detect or determine characteristics of the chemical reaction. The threshold voltage may for example be measured by applying appropriate bias voltages to the source and drain, and measuring a resulting current flowing through the chemFET. As another example, the threshold voltage may be measured by driving a known current through the chemFET, and measuring a resulting voltage at the source or drain.

An ion-sensitive field effect transistor (ISFET) is a type of chemFET that includes an ion-sensitive layer at the sensitive area. The presence of ions in an analyte solution alters the surface potential at the interface between the ion-sensitive layer and the analyte solution, due to the protonation or deprotonation of surface charge groups caused by the ions present in the analyte solution. The change in surface potential at the sensitive area of the ISFET affects the threshold voltage of the device, which can be measured to indicate the presence and/or concentration of ions within the solution. Arrays of ISFETs may be used for monitoring chemical reactions, such as DNA sequencing reactions, based on the detection of ions present, generated, or used during the reactions. See, for example, Rothberg et al., U.S. Ser. No. 12/002,291 (now U.S. Pat. No. 7,948,015), filed Dec. 14, 2009, which is incorporated by reference herein in its entirety. More generally, large arrays of chemFETs or other types of chemical sensors may be employed to detect and measure static or dynamic amounts or concentrations of a variety of analytes (e.g. hydrogen ions, other ions, compounds, etc.) in a variety of processes. The processes may for example be biological or chemical reactions, cell or tissue cultures or monitoring neural activity, nucleic acid sequencing, etc.

An issue that arises in the operation of large scale chemical sensor arrays is the susceptibility of the sensor output signals to noise. Specifically, the noise affects the accuracy of the downstream signal processing used to determine the characteristics of the chemical or biological process being detected by the sensors. In addition, chemical sensor performance variation across the array results in undesirable differences in the sensor output signals, which further complicates the downstream signal processing. It is therefore desirable to provide devices including low noise chemical sensors, and methods for manufacturing such devices.

BRIEF DESCRIPTION OF THE DRAWINGS

The present disclosure may be better understood, and its numerous features and advantages made apparent to those skilled in the art by referencing the accompanying drawings.

The use of the same reference symbols in different drawings indicates similar or identical items.

DETAILED DESCRIPTION

A chemical detection device is described that includes low noise chemical sensors, such as chemically-sensitive field effect transistors (chemFETs), for detecting chemical reactions within overlying, operationally associated reaction regions.

Figure 1:
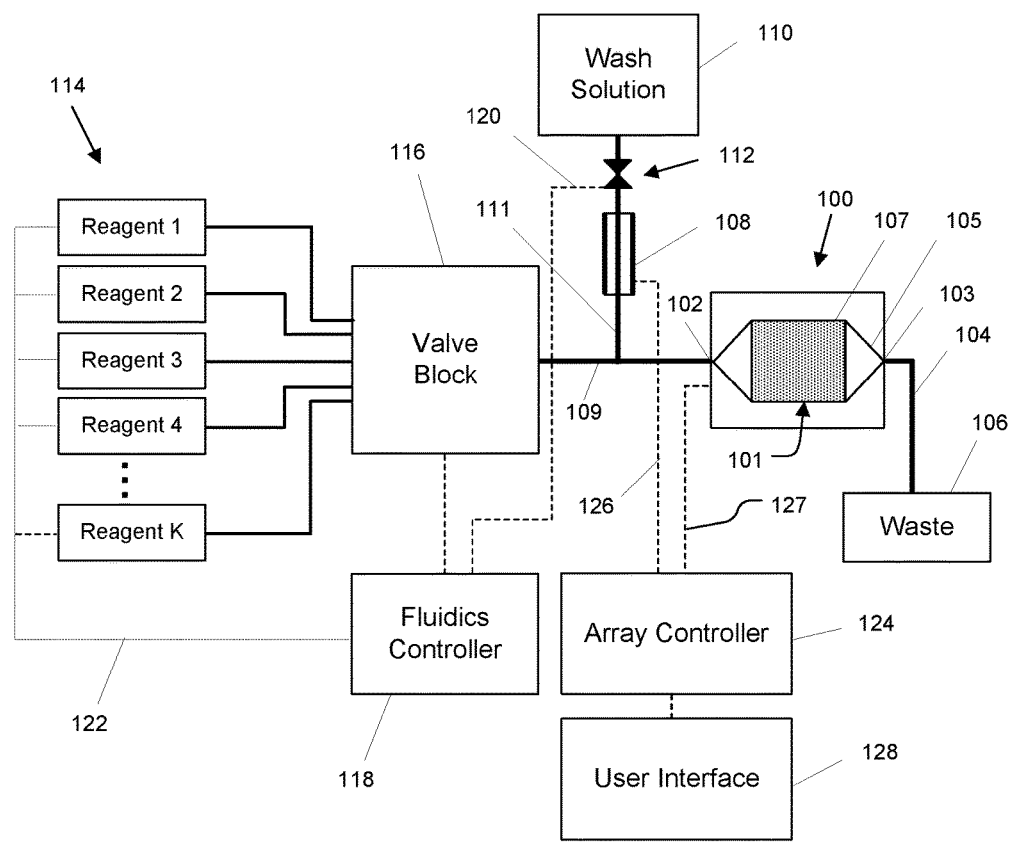
FIG. 1 illustrates a block diagram of components of a system for nucleic acid sequencing according to an exemplary embodiment.

FIG. 1 illustrates a block diagram of components of a system for nucleic acid sequencing according to an exemplary embodiment. The components include a flow cell 101 on an integrated circuit device 100, a reference electrode 108, a plurality of reagents 114 for sequencing, a valve block 116, a wash solution 110, a valve 112, a fluidics controller 118, lines 120/122/126, passages 104/109/111, a waste container 106, an array controller 124, and a user interface 128. The integrated circuit device 100 includes a microwell array 107 overlying a sensor array that includes chemical sensors as described herein. The flow cell 101 includes an inlet 102, an outlet 103, and a flow chamber 105 defining a flow path for the reagents 114 over the microwell array 107. The reference electrode 108 may be of any suitable type or shape, including a concentric cylinder with a fluid passage or a wire inserted into a lumen of passage 111. The reagents 114 may be driven through the fluid pathways, valves, and flow cell 101 by pumps, gas pressure, vacuum, or other suitable methods, and may be discarded into the waste container 106 after exiting the outlet 103 of the flow cell 101. The fluidics controller 118 may control driving forces for the reagents 114 and the operation of valve 112 and valve block 116 with suitable software.

The microwell array 107 includes reaction regions, also referred to herein as microwells, which are operationally associated with corresponding chemical sensors in the sensor array. For example, each reaction region may be coupled to a chemical sensor suitable for detecting an analyte or reaction property of interest within that reaction region. The microwell array 107 may be integrated in the integrated circuit device 100, so that the microwell array 107 and the sensor array are part of a single device or chip. The flow cell 101 may have a variety of configurations for controlling the path and flow rate of reagents 114 over the microwell array 107. The array controller 124 provides bias voltages and timing and control signals to the integrated circuit device 100 for reading the chemical sensors of the sensor array. The array controller 124 also provides a reference bias voltage to the reference electrode 108 to bias the reagents 114 flowing over the microwell array 107.

In operation, the array controller 124 collects and processes output signals from the chemical sensors of the sensor array through output ports on the integrated circuit device 100 via bus 127. The array controller 124 may be a computer or other computing means. The array controller 124 may include memory for storage of data and software applications, a processor for accessing data and executing applications, and components that facilitate communication with the various components of the system in FIG. 1. In the illustrated embodiment, the array controller 124 is external to the integrated circuit device 100. In some alternative embodiments, some or all of the functions performed by the array controller 124 are carried out by a controller or other data processor on the integrated circuit device 100. The values of the output signals from the chemical sensors indicate physical or chemical parameters of one or more reactions taking place in the corresponding reaction regions in the microwell array 107. The user interface 128 may display information about the flow cell 101 and the output signals received from chemical sensors in the sensor array on the integrated circuit device 100. The user interface 128 may also display instrument settings and controls, and allow a user to enter or set instrument settings and controls.

In some embodiments, the fluidics controller 118 may control delivery of the individual reagents 114 to the flow cell 101 and integrated circuit device 100 in a predetermined sequence, for predetermined durations, at predetermined flow rates. The array controller 124 can then collect and analyze the output signals of the chemical sensors indicating chemical reactions occurring in response to the delivery of the reagents 114. During the experiment, the system may also monitor and control the temperature of the integrated circuit device 100, so that reactions take place and measurements are made at a known predetermined temperature.

The system may be configured to let a single fluid or reagent contact the reference electrode 108 throughout an entire multi-step reaction during operation. The valve 112 may be shut to prevent any wash solution 110 from flowing into passage 109 as the reagents 114 are flowing. Although the flow of wash solution may be stopped, there may still be uninterrupted fluid and electrical communication between the reference electrode 108, passage 109, and the microwell array 107. The distance between the reference electrode 108 and the junction between passages 109 and 111 may be selected so that little or no amount of the reagents flowing in passage 109 (and possibly diffusing into passage 111) reaches the reference electrode 108. In an exemplary embodiment, the wash solution 110 may be selected as being in continuous contact with the reference electrode 108, which may be especially useful for multi-step reactions using frequent wash steps.

Figure 2:
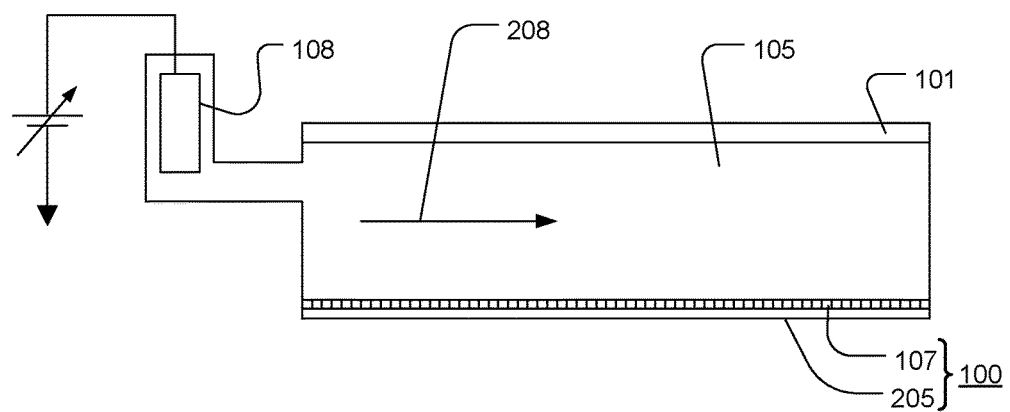
FIG. 2 illustrates a cross-sectional view of a portion of the integrated circuit device and flow cell according to an exemplary embodiment.

FIG. 2 illustrates cross-sectional and expanded views of a portion of the integrated circuit device 100 and flow cell 101. The integrated circuit device 100 includes the microwell array 107 of reaction regions operationally associated with sensor array 205. During operation, the flow chamber 105 of the flow cell 101 confines a reagent flow 208 of delivered reagents across open ends of the reaction regions in the microwell array 107. The volume, shape, aspect ratio (such as base width-to-well depth ratio), and other dimensional characteristics of the reaction regions may be selected based on the nature of the reaction taking place, as well as the reagents, byproducts, or labeling techniques (if any) that are employed. The chemical sensors of the sensor array 205 are responsive to (and generate output signals related to) chemical reactions within associated reaction regions in the microwell array 107 to detect an analyte or reaction property of interest. The chemical sensors of the sensor array 205 may for example be chemically sensitive field-effect transistors (chemFETs), such as ion-sensitive field effect transistors (ISFETs).

Provided herein is a device for detecting a reaction. The reaction may be localized to a reaction region and multiple reactions of the same type may occur in the same reaction region. The reaction that may occur may be a chemical reaction that results in the detection of a reaction by-product or the detection of a signal indicating a reaction. A sensor may be located in proximity to the reaction region and may detect the reaction by-product or the signal. The sensor may be a CMOS type of sensor. In some embodiments, the sensor may detect a hydrogen ion, hydroxide ion, or the release of pyrophosphate. In some embodiments, the sensor may detect the presence of a dye molecule.

Figure 3:
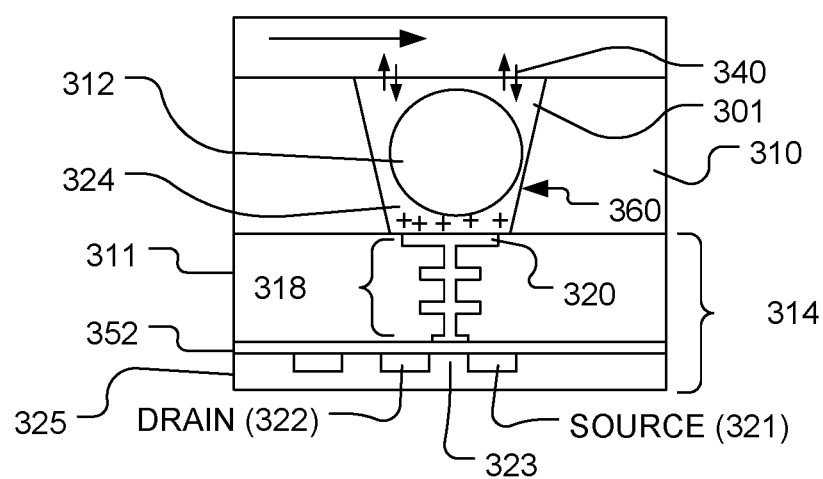
FIG. 3 illustrates a cross-sectional view of two representative chemical sensors and their corresponding reaction regions according to a first embodiment.

FIG. 3 illustrates a representative reaction region 301 and a chemical sensor 314. The reaction region may be an opening such as a well, depression, or channel. Alternatively, the reaction region may be an area where any suitable reaction takes place. A sensor array may have millions of these chemical sensors 314 and reaction regions 301. The chemical sensor 314 may be a chemically-sensitive field effect transistor (chemFET), or more specifically an ion-sensitive field effect transistor (ISFET). The chemical sensor 314 includes a floating gate structure 318 having a sensor plate 320 coupled to a reaction region 301 via an electrically conductive layer within the reaction region 301. The floating gate structure 318 may include multiple layers of conductive material within layers of dielectric material or may include a single layer of conductive material within a single layer of dielectric material 311. The chemical sensor may include a source 321 and a drain 322 located within the substrate. The source 321 and the drain 322 include doped semiconductor material having a conductivity type different from the conductivity type of the substrate. For example, the source 321 and the drain 322 may comprise doped P-type semiconductor material, and the substrate may comprise doped N-type semiconductor material. A channel 323 separates the source 321 and the drain 322. The floating gate structure 318 overlies the channel region 323, and is separated from the substrate by a gate dielectric 352. The gate dielectric 352 may be for example silicon dioxide. Alternatively, other dielectrics may be used for the gate dielectric 352.

As shown in FIG. 3, the reaction region 301 is within an opening extending through dielectric materials 310 to the upper surface of the sensor plate 320. The dielectric material 310 may comprise one or more layers of material, such as silicon dioxide or silicon nitride. The opening also includes an upper portion 315 within the dielectric material 310 and extending from the lower portion 314 to the upper surface of the dielectric material 310. In some embodiments, the width of the upper portion of the opening is substantially the same as the width of the lower portion of the reaction region. Alternatively, depending on the material(s) or etch process used to create the opening, the width of the upper portion of the opening may be greater than the width of the lower portion of the opening, or vice versa. The opening may for example have a circular cross-section. Alternatively, the opening may be non-circular. For example, the cross-section may be square, rectangular, hexagonal, or irregularly shaped. The dimensions of the openings, and their pitch, can vary from embodiment to embodiment. In some embodiments, the openings can have a characteristic diameter, defined as the square root of 4 times the plan view cross-sectional area (A) divided by Pi (e.g., sqrt(4*A/π)), of not greater than 5 micrometers, such as not greater than 3.5 micrometers, not greater than 2.0 micrometers, not greater than 1.6 micrometers, not greater than 1.0 micrometers, not greater than 0.8 micrometers, not greater than 0.6 micrometers, not greater than 0.4 micrometers, not greater than 0.2 micrometers or even not greater than 0.1 micrometers, but, optionally, at least 0.001 micrometers, such as at least 0.01 micrometers.

In some embodiments, during manufacturing or operation of the device, a thin oxide of the material of the electrically conductive material may be grown which acts as a sensing material (e.g. an ion-sensitive sensing material) for the chemical sensor. Whether an oxide is formed depends on the conductive material, the manufacturing processes performed, and the conditions under which the device is operated. For example, in some embodiments the electrically conductive element may be titanium nitride, and titanium oxide or titanium oxynitride may be grown on the inner surface of the conductive material during manufacturing or during exposure to solutions during use. The electrically conductive element may comprise one or more layers of a variety of electrically conductive materials, such as metals or ceramics. The conductive material can be for example a metallic material or alloy thereof, or can be a ceramic material, or a combination thereof. An exemplary metallic material includes one of aluminum, copper, nickel, titanium, silver, gold, platinum, hafnium, lanthanum, tantalum, tungsten, iridium, zirconium, palladium, or a combination thereof. An exemplary ceramic material includes one of titanium nitride, titanium aluminum nitride, titanium oxynitride, tantalum nitride or a combination thereof. In some alternative embodiments, an additional conformal sensing material is deposited on the conductive element and within the openings. The sensing material may comprise one or more of a variety of different materials to facilitate sensitivity to particular ions. For example, silicon nitride or silicon oxynitride, as well as metal oxides such as silicon oxide, aluminum or tantalum oxides, generally provide sensitivity to hydrogen ions, whereas sensing materials comprising polyvinyl chloride containing valinomycin provide sensitivity to potassium ions. Materials sensitive to other ions such as sodium, silver, iron, bromine, iodine, calcium, and nitrate may also be used, depending upon the embodiment.

In operation, reactants, wash solutions, and other reagents may move in and out of the reaction region 301 by a diffusion mechanism 340. The chemical sensor 314 is responsive to (and generates an output signal related to) the amount of charge 324 proximate to the sensor plate 320. The presence of charge 324 in an analyte solution alters the surface potential at the interface between the sensor plate 320 and the analyte solution within the reaction region 301. Changes in the charge 324 cause changes in the voltage on the floating gate structure 318, which in turn changes in the threshold voltage of the transistor. This change in threshold voltage can be measured by measuring the current in the channel region 323 between the source 321 and a drain 322. As a result, the chemical sensor 314 can be used directly to provide a current-based output signal on an array line connected to the source 321 or drain 322, or indirectly with additional circuitry to provide a voltage-based output signal.

In some embodiments, reactions carried out in the reaction region 301 can be analytical reactions to identify or determine characteristics or properties of an analyte of interest. Such reactions can generate directly or indirectly byproducts that affect the amount of charge adjacent sensor plate 320 or any other materials or coatings that may be placed on the sensor plate to increase conductivity. If such byproducts are produced in small amounts or rapidly decay or react with other constituents, multiple copies of the same analyte may be analyzed in the reaction region 301 at the same time in order to increase the output signal generated. In some embodiments, multiple copies of an analyte may be attached to a solid phase support 312, as shown in FIG. 3, either before or after deposition into the reaction region 301. The solid phase support 312 may be a particle, microparticle, nanoparticle, or bead. The solid phase support may be solid or porous or may be a gel, or a combination thereof. The solid support may be a structure located in the middle of the reaction region. Alternatively, the solid support may be located at the bottom of the reaction region. For a nucleic acid analyte, multiple, connected copies may be made by rolling circle amplification (RCA), exponential RCA, Recombinase Polymerase Amplification (RPA), Polymerase Chain Reaction amplification (PCR), emulsion PCR amplification, or like techniques, to produce an amplicon without the need of a solid support.

In various exemplary embodiments, the methods, systems, and computer readable media described herein may advantageously be used to process or analyze data and signals obtained from electronic or charged-based nucleic acid sequencing. In electronic or charged-based sequencing (such as, pH-based sequencing), a nucleotide incorporation event may be determined by detecting ions (e.g., hydrogen ions) that are generated as natural by-products of polymerase-catalyzed nucleotide extension reactions. This detection method may be used to sequence a sample or template nucleic acid, which may be a fragment of a nucleic acid sequence of interest, for example, and which may be directly or indirectly attached as a clonal population to a solid support, such as a particle, microparticle, bead, etc. The sample or template nucleic acid may be operably associated to a primer and polymerase and may be subjected to repeated cycles or "flows" of deoxynucleoside triphosphate ("dNTP") addition (which may be referred to herein as "nucleotide flows" from which nucleotide incorporations may result) and washing. The primer may be annealed to the sample or template so that the primer's 3' end can be extended by a polymerase whenever dNTPs complementary to the next base in the template are added. Then, based on the known sequence of nucleotide flows and on measured output signals of the chemical sensors indicative of ion concentration during each nucleotide flow, the identity of the type, sequence and number of nucleotide(s) associated with a sample nucleic acid present in a reaction region coupled to a chemical sensor can be determined.

Provided herein is a chemical sensor comprising a chemically-sensitive field effect transistor (chemFET) including a floating gate conductor having an upper surface. At least a first material located on top of the chemFET either in proximity to or on top of the floating gate conductor and a second material located on top of the first material. The chemical sensor has a first opening is etched into the chemical sensor and the first opening may extend completely through the second material and may then extend a portion of the first material. In addition, the second material may have a second opening. The second opening may be located anywhere beneath the first opening but may be located in the center of the bottom of the first opening. The second opening extends from the bottom surface of the first opening to the top of a lining layer on the metal layer. The first material may be a dielectric material. The second material may be an oxide, such as silicon oxide. In some embodiments, the second opening of the chemical sensor may be similar in size to the first opening. In some embodiments, the second opening of the chemical sensor may have a smaller area or circumference than the area or circumference of the first opening of the chemical sensor. The width of the lower portion of the second opening may be substantially the same as the width of the upper portion of the second opening or the upper portion may be wider than the lower portion of the second opening. Likewise, the width of the lower portion of the first opening may be substantially the same as the width of the upper portion of the first opening or alternatively, the upper portion may be wider than the lower portion of the first opening. In some embodiments, the chemical sensor may include a biocompatible layer. The biocompatible layer may be located on or in the bottom of the first opening but not on or in the second opening or the biocompatible layer may be located on or in the second opening but not on or in the first opening. Alternatively, the biocompatible layer may be located on or in the first opening and on or in the second opening. The biocompatible layer may be located on the entire surface of the first, second or both first and second opening or may be located on at least a portion of the first, second, or both first and second opening. The biocompatible layer may be located on the bottom of the openings or on the sidewalls of the openings. Additionally, the chemical sensor may further include an electrically conductive layer over at least a portion of the first, second, or both first and second opening. The electrically conductive layer may be located on or in the bottom of the first opening but not on or in the second opening or the electrically conductive layer may be located on or in the second opening but not on or in the first opening. Alternatively, the electrically conductive layer may be located on or in the first opening and on or in the second opening. The electrically conductive layer may be located on the entire surface of the first, second or both first and second opening or may be located on at least a portion of the first, second, or both first and second opening. The electrically conductive layer may be located on the bottom of the openings or on the sidewalls of the openings. The opening may be a well, such as a microwell or nanowell, but it may also be a channel, depression, indent or any other suitable structure for a reaction region.

Further provided herein is a method for manufacturing a chemical sensor. In some embodiments, the method may include providing or forming a chemically-sensitive field effect transistor including a floating gate conductor having an upper surface. A metal material is then deposited either on top of or in proximity to the upper surface of the floating gate conductor. On top of the metal layer, an unreactive material or liner layer is deposited. The unreactive material is one that is not removed by during the removal of the filler material, such that the metal layer remains unaffected by and chemical clean steps. The liner layer can be any suitable unreactive material, such as titanium nitride. A first material is then deposited on the metal layer where present on the chemical sensor and any area not covered by metal. The method further provides for forming a first opening in the first material where the first opening extends from the upper surface of the floating gate conductor to the top of the first material. The first material may be an oxide, such as silicon oxide. The first opening is then, according to the method, filled with a filler material. The filler material may be a metal, such as tungsten. The filler material may be any material that is not etched by the same etching process for forming the second opening. After the filler material is deposited in the opening, a second material may be deposited over the upper surface of the first material and the filler material. The second material may be a dielectric such as silicon nitride. Further provided for in the method is forming a second opening in the structure. The second opening extends through the depth of the second material. In some embodiments, the second opening has a top surface that is at the upper surface of the second material and a lower surface that is located at the bottom of the second opening. The lower surface may be the same as the top surface of the first material. Alternatively, the second opening may extend through the entire second material and may also extend through a portion of the first material. The extent to which the first material is etched with the second material may be a predetermined depth. The filler material however, is not etched during this etching process and therefore may extend in the negative space created during the second etch of the first and second material. Finally, the filler material may be removed during a separate clean-up step leaving the first opening and the second opening. The first and second openings may be a well, such as a microwell, nanowell, indent, depression, or channel or combination thereof. The forming of the second opening may include etching the first material and the second material during the same etch step. Alternatively, the first and second materials may be etched during different steps. In some embodiments, the second opening of the chemical sensor may be similar in size to the first opening. In some embodiments, the first opening of the chemical sensor may have a smaller area or circumference than the area or circumference of the second opening of the chemical sensor. The width of the lower portion of the second opening may be substantially the same as the width of the upper portion of the second opening or the upper portion may be wider than the lower portion of the second opening. Likewise, the width of the lower portion of the first opening may be substantially the same as the width of the upper portion of the first opening or alternatively, the upper portion may be wider than the lower portion of the first opening. The area of the second opening may have a larger area than the first opening. In some embodiments of the method provided herein, the method may further include depositing a biocompatible layer, an electrically conductive layer, or both a biocompatible and electrically conductive layer.

Figure 4:
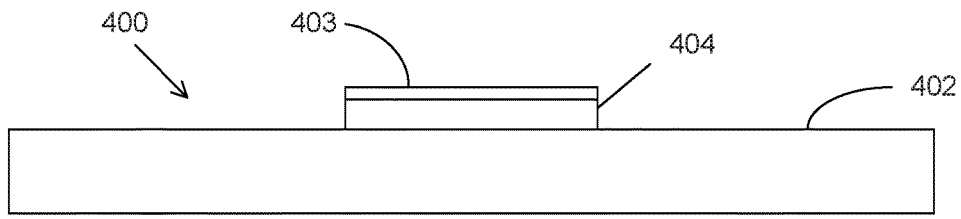
FIGS. 4 to 10 illustrate stages in a manufacturing process for forming an array of chemical sensors and corresponding reaction regions according to a first embodiment.
Figure 8:
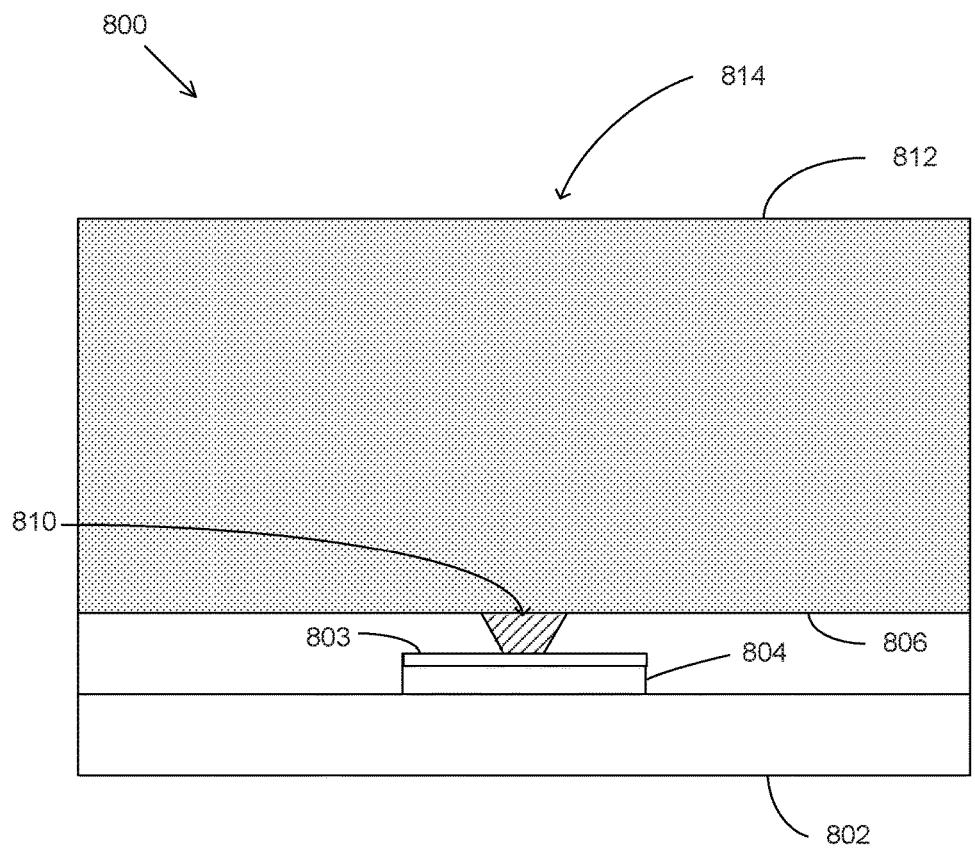
Figure 9:
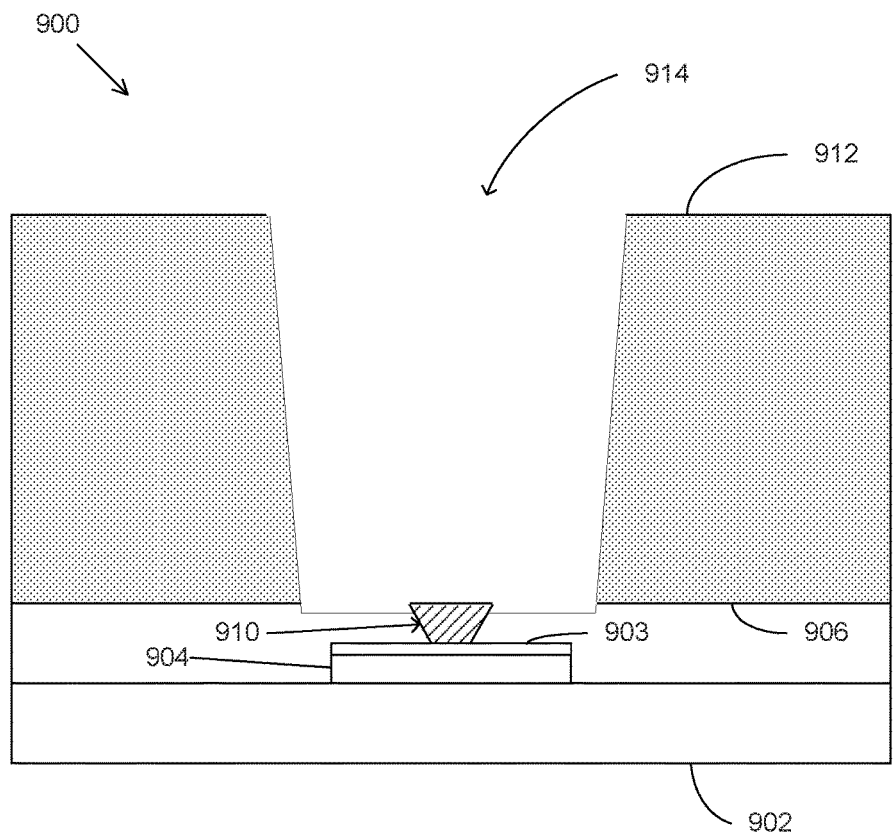
Figure 10:
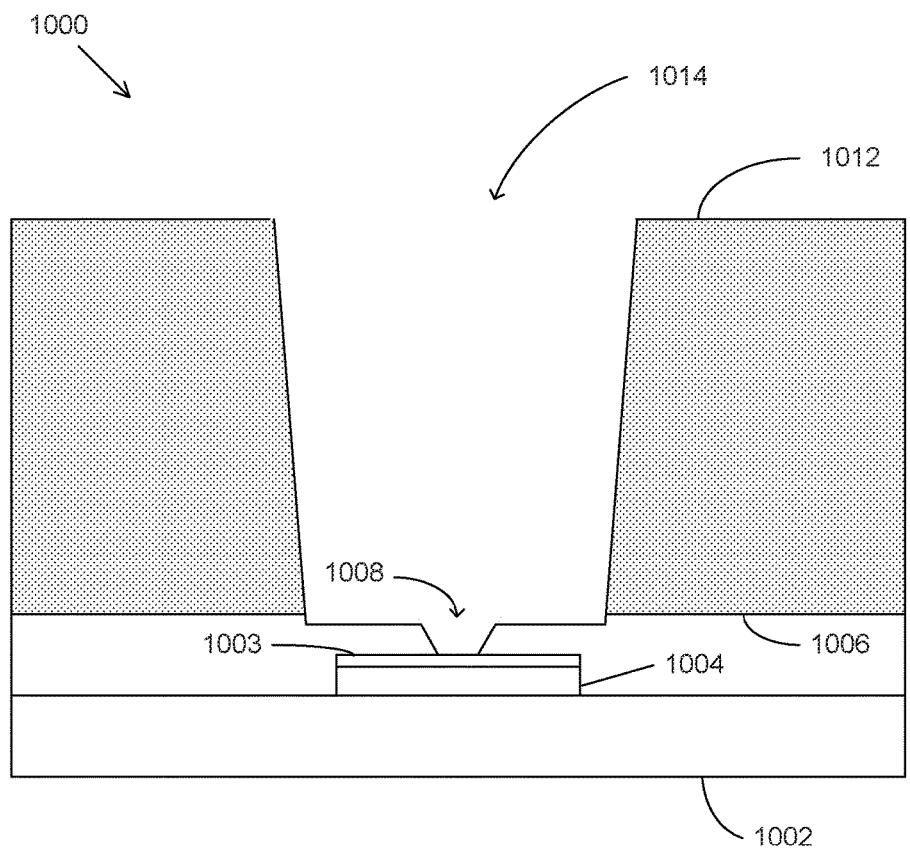

FIGS. 4 to 10 illustrate one embodiment of the stages in a manufacturing process for forming an array of chemical sensors and corresponding reaction region. FIG. 4 shows a structure 400 including a substrate 402 and a metal layer 404. The substrate layer 402 may be any suitable semiconductor material layer, for example silicon oxide. The substrate layer may include a floating gate structure as describe previously above. The metal layer 404 which will be located under the air via, as shown in FIG. 10, may be deposited and patterned on the substrate layer 402 using standard lithography and etch protocols. The metal layer may be any suitable electrically conductive material including but not limited to aluminum copper alloy, aluminum, copper, titanium, tantalum, hafnium, zinc, tungsten, gold, platinum, or silver, or any combination thereof. The top surface (or optional liner layer) 403 of the metal layer may be any suitable material that is not removed by the subsequent air via removal process, such as titanium nitride for example, but any suitable liner layer may be used. The metal layer 404 may be deposited over floating gates formed within the substrate 402. The floating gates may be multi-layer metal floating gates. Alternatively, the metal layer may be disposed over the gate dielectric or a single conductor layer over the gate dielectric.

Figure 5:
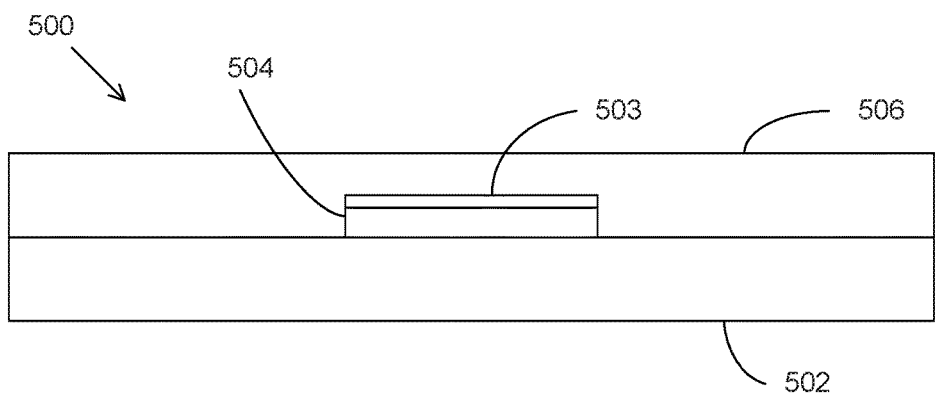

After the metal layer 504 is deposited on the substrate, an oxide layer 506 is deposited over the liner layer 503 or top surface of the metal layer 504 and the substrate layer 502 as shown in the structure 500 of FIG. 5. The oxide layer will form the air via and may be referred to the air via oxide layer. The oxide layer may be silicon oxide or any other suitable oxide layer. After the oxide layer 506 is deposited on the liner layer 503 of the metal layer 504 and the substrate layer 502, the oxide layer 506 is then flattened by any suitable means including, but not limited to, chemical mechanical polish (CMP) using standard deposition and CMP protocols.

Figure 6:
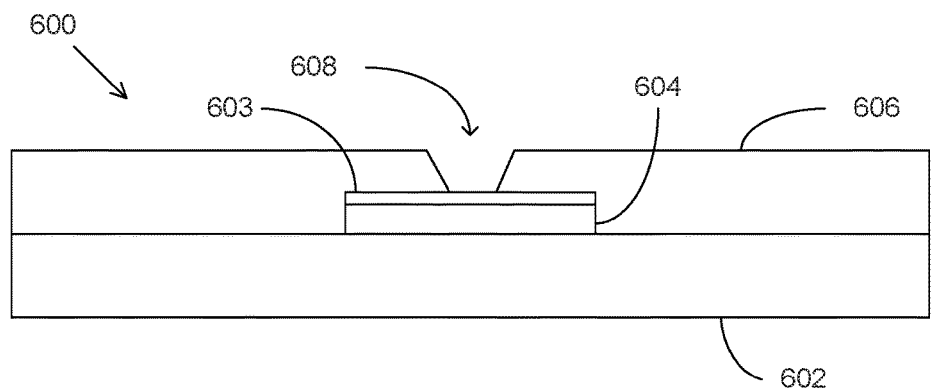

After the oxide layer 606 is deposited on the substrate 602 and the liner layer 603 of the metal 604 of the structure 600 and flattened, the oxide layer 606 is patterned and then etched using standard via etch protocols including but not limited to photolithographic etching techniques. For example, a layer of photoresist may be patterned on the dielectric material to define the locations of the openings and then anisotropically etching the dielectric material using the patterned photoresist as an etch mask. The anisotropic etching of the dielectric material may, for example, be a dry etch process, such as a fluorine based Reactive Ion Etching (RIE) process. The air via oxide layer is then etched to the surface of the liner layer 603 on the metal layer 604 and results in an "air via" 608 as shown in FIG. 6.

Figure 7:
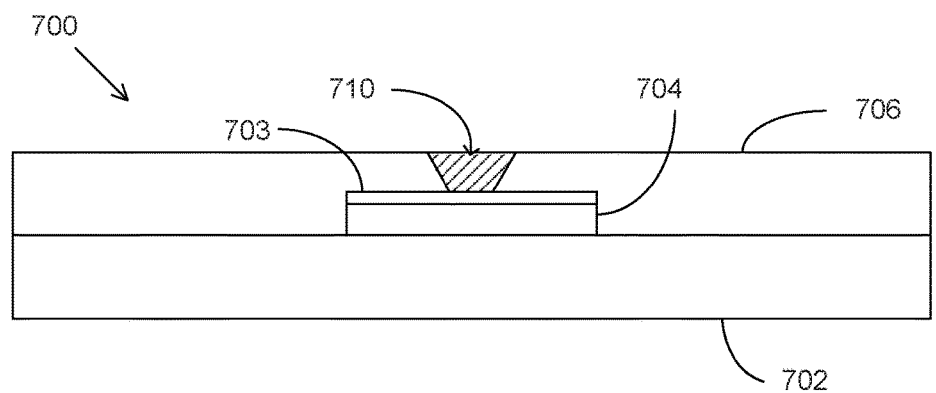

FIG. 7 shows the structure 700 including a substrate 702, liner layer 703 on top of the metal layer 704, and oxide layer 706. After the air via 608 is formed, it is then filled with a filler material 710 as shown in FIG. 7. In some embodiments, the via may be filled with tungsten, titanium, tantalum, or any other suitable filler material such that the filler material is not etched or does not react during the subsequent micro well etch process but is capable of being removed by post micro well etch clean up step. The filler material 710 may be deposited by sputtering, atomic layer deposition (ALD), low pressure vapor deposition (LPCVD), plasma enhanced chemical vapor deposition (PECVD), metal organic chemical vapor deposition (MOCVD) or any other suitable deposition technique. After filling the via with the filler material 710, the filler material 710 is flattened using standard via processing protocols, for example CMP methods. The top surface of the filler material 710 may be flattened to be substantially planar with the air via oxide layer 706. In some embodiments, more than one layer of filler material may be deposited in the via or more than one type of material may be deposited.

After the conductive material 810 is flattened to be substantially planar with the oxide layer 806 of the structure 800, a dielectric material 812 may be deposited over the oxide layer 806 and the conductive material 810 as shown in FIG. 8. The dielectric material 812 may be tetraethyl orthosilicate (TEOS), plasma enhanced silicon oxide (PEOX), silicon nitride, or other silicon dioxide embodiments, amorphous undoped silicon, or any suitable material. The dielectric material may be a single layer of one type of material or a plurality of multiple layers of materials.

The dielectric material 912 is then etched as shown in FIG. 9 to create a well 914 in the dielectric material 912. The dielectric material 912 may be etched to the surface of the oxide layer 906 and the surface of the conductive material 910 using a suitable etching chemical. Alternatively, the microwell etch may etch into the oxide layer 906 as shown in FIG. 9 such that the conductive material 910 may extend past the surface of the oxide layer 906. In such an embodiment, the fill material extending past the surface of the air via layer may be removed subsequent to processing. The depth of the etch and whether the etch includes etch of the oxide layer may be predefined.

After the etch of the dielectric material 1012 has occurred, a post etch clean out step is carried out to remove any unwanted left over polymer in the well cavity 1014. During this process, the conductive material (shown as 910 in FIG. 9) previously deposited in the via 1008 may be removed as well as shown in FIG. 10. The clean out chemistry used in this step should be such that the metals are removed but not any portion of the oxide layers. This clean out may be performed with fluorine or chlorine based acids, for example. The liner layer 1003 on top of the metal layer protects the metal layer 1004 from reacting during the etch process. After the post microwell etch clean is completed an air via 1008 is located at the bottom of the well 1014. In some embodiment, an additional layer of material may be deposited. The material may be deposited just at the bottom of the well and may include the surface area of the air via or the material may be deposited on the side walls of the well. Alternatively, the material may be deposited either fully or at least partially on all surfaces of the well.

Provided herein is a chemical sensor comprising a chemically-sensitive field effect transistor including a floating gate conductor having an upper surface, a first opening extending through a first material and through a portion of a second material, and a second opening extending from the bottom of the first opening to the top of a metal layer located on the upper surface of the floating gate conductor. The first material may be a dielectric material. The second material may be an oxide, such as silicon oxide. The second opening of the chemical sensor may have a smaller surface area than the first opening of the chemical sensor. In some embodiments, the width of the lower portion of the second opening is substantially the same as the width of the upper portion of the second opening. In some embodiments, the chemical sensor may include a biocompatible layer on at least a portion of the first, second, or both first and second opening. The biocompatible layer may include any suitable biocompatible material or biological structures that may be useful in detecting a biological event. Additionally, the chemical sensor may further include an electrically conductive layer over at least a portion of the first, second, or both first and second opening. The opening may be a well and the bottom of the first opening may be the same surface as the top of the second opening.

Further provided herein is a method for manufacturing a chemical sensor, the method including forming a chemically-sensitive field effect transistor including a floating gate conductor having an upper surface, forming a first opening in a first material extending from the upper surface of the floating gate conductor, filling the first opening with a filler material, forming a second opening extending through a portion of the first material and through a second material extending, and removing the filler material from the first opening. The filler material may be tungsten. The opening may be a well. The method provided herein may include forming the first opening which may further include forming an oxide layer on the floating gate conductor and etching a portion of the oxide layer to the upper surface of the floating gate conductor. Additionally, forming the second opening may include depositing a dielectric on the surface of the oxide layer and the metal, etching the dielectric layer, and etching a portion of the oxide layer. The etching process may include etching to the top surface, for example an oxide layer, of the first material or may alternatively include etching past the top surface of the first material a predetermined depth. The etching of a portion of the oxide layer may include etching below the top surface of the filler material. The filler material may be a metal material. The forming of the opening may include etching the first material and the second material during the same etch step. Alternatively, the first and second materials may be etched during a different step. The area of the second opening may have a larger area than the first opening.

In a first aspect, a method for manufacturing a chemical sensor includes forming a chemically-sensitive field effect transistor including a floating gate conductor having an upper surface; forming a metal layer on the upper surface; forming a first opening in a first material extending from the upper surface of the first material to the metal layer; filling the first opening with a filler material; forming a second opening extending through a second material and a portion of the first material; and removing the filler material from the first opening.

In an example of the first aspect, the method further includes forming a liner layer on the metal layer prior to forming an opening in the first material. For example, the liner layer includes titanium nitride.

In another example of the first aspect and the above examples, forming the first opening includes forming the first material over the floating gate conductor and the metal layer, the first material comprising an insulator; and etching a portion of the first material to the metal layer. For example, the insulator includes an oxide.

In a further example of the first aspect and the above examples, forming the second opening includes depositing the second material on the surface of the first material and the filler material; and etching the second material. For example, the method further includes etching a portion of the first material. In an example, the etching of the portion of the first material includes etching below the top surface of the filler material. In an additional example, the second material includes a dielectric material. In another example, the dielectric material includes a nitride or oxide of silicon.

In an additional example of the first aspect and the above examples, the forming the second opening includes etching the first material and the second material during the same etch step.

In another example of the first aspect and the above examples, the filler material is tungsten.

In a further example of the first aspect and the above examples, the second opening is a well.

In an additional example of the first aspect and the above examples, forming the second opening includes forming an opening having a larger area than the area of the first opening.

In a second aspect, a chemical sensor includes a chemically-sensitive field effect transistor including a floating gate conductor having an upper surface; a first opening extending through a first material and through a portion of a second material; and a second opening extending from the bottom of the first opening to the top of a liner layer on a metal layer located on the upper surface of the floating gate conductor.

In an example of the second aspect, the first material is a dielectric material.

In another example of the second aspect and the above examples, the second opening has a smaller area than the area of the first opening.

In further example of the second aspect and the above examples, a width of the lower portion of the first opening is substantially the same as a width of the upper portion of the first opening.

In additional example of the second aspect and the above examples, a biocompatible layer is deposited on at least a portion of the first and second opening.

In another example of the second aspect and the above examples, the chemical sensor further includes an electrically conductive layer.

In a further example of the second aspect and the above examples, second opening is a well.

In an additional example of the second aspect and the above examples, the second material is an oxide. For example, the oxide is silicon oxide.

In another example of the second aspect and the above examples, the top of the second opening is the same as the bottom of the first opening.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

As used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

Also, the use of "a" or "an" are employed to describe elements and components described herein. This is done merely for convenience and to give a general sense of the scope of the invention. This description should be read to include one or at least one and the singular also includes the plural unless it is obvious that it is meant otherwise.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

After reading the specification, skilled artisans will appreciate that certain features are, for clarity, described herein in the context of separate embodiments, may also be provided in combination in a single embodiment. Conversely, various features that are, for brevity, described in the context of a single embodiment, may also be provided separately or in any subcombination. Further, references to values stated in ranges include each and every value within that range.

While the present invention is disclosed by reference to the preferred embodiments and examples detailed above, it is to be understood that these examples are intended in an illustrative rather than in a limiting sense. It is contemplated that modifications and combinations will readily occur to those skilled in the art, which modifications and combinations will be within the spirit of the invention and the scope of the following claims.

What is claimed is:

1. A method for manufacturing a chemical sensor, the method comprising:
    forming a chemically-sensitive field effect transistor including a floating gate conductor having an upper surface;
    forming a metal layer on the upper surface;
    forming a first material over the floating gate conductor and the metal layer, the first material comprising an insulator;
    forming a first opening in the first material extending from the upper surface of the first material to the metal layer by anisotropically etching a portion of the first material to the metal layer;
    filling the first opening with a filler material including tungsten, titanium, or tantalum, the filler in direct contact with the first material;
    depositing a second material on the surface of the first material and the filler material;
    forming a second opening extending through the second material and a portion of the first material by etching the second material and a portion of the first material below a top surface of the filler material to expose the filler material in a void left by the etched portion of the first material; and
    removing the filler material from the first opening.

2. The method of claim 1, further comprising:
    forming a liner layer on the metal layer prior to forming an opening in the first material.

3. The method of claim 2, wherein the liner layer includes titanium nitride.

4. The method of claim 1, wherein the insulator includes an oxide.

5. The method of claim 1, wherein the second material includes a dielectric material.

6. The method of claim 5, wherein the dielectric material includes a nitride or oxide of silicon.

7. The method of claim 1, wherein the forming the second opening includes etching the first material and the second material during the same etch step.

8. The method of claim 1, wherein the second opening is a well.

9. The method of claim 1, wherein forming the second opening includes forming an opening having a larger area than the area of the first opening.

* * * * *